United States Patent
Kurze

(10) Patent No.: US 9,474,502 B2
(45) Date of Patent: Oct. 25, 2016

(54) CONTROL FOR OPTICALLY ALIGNING AN X-RAY TUBE AND X-RAY DETECTOR

(71) Applicant: KONINKLIJKE PHILIPS N.V., Eindhoven (NL)

(72) Inventor: Christoph Kurze, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 234 days.

(21) Appl. No.: 14/361,574

(22) PCT Filed: Nov. 26, 2012

(86) PCT No.: PCT/IB2012/056716
§ 371 (c)(1),
(2) Date: May 29, 2014

(87) PCT Pub. No.: WO2013/080111
PCT Pub. Date: Jun. 6, 2013

(65) Prior Publication Data
US 2014/0341356 A1    Nov. 20, 2014

Related U.S. Application Data

(60) Provisional application No. 61/565,545, filed on Dec. 1, 2011.

(51) Int. Cl.

| | | |
|---|---|---|
| *A61B 6/08* | (2006.01) | |
| *A61N 5/10* | (2006.01) | |
| *H01J 37/22* | (2006.01) | |
| *G02B 27/64* | (2006.01) | |
| *A61B 6/00* | (2006.01) | |
| *A61B 6/04* | (2006.01) | |
| *G02B 7/00* | (2006.01) | |
| *H04B 10/00* | (2013.01) | |

(52) U.S. Cl.
CPC ............ *A61B 6/587* (2013.01); *A61B 6/0492* (2013.01); *A61B 6/08* (2013.01); *A61B 6/4405* (2013.01); *A61B 6/461* (2013.01); *A61B 6/547* (2013.01); *A61N 5/1049* (2013.01); *G02B 7/005* (2013.01); *G02B 27/64* (2013.01); *H01J 37/22* (2013.01); *A61B 6/4411* (2013.01); *A61B 6/4452* (2013.01); *A61B 6/4464* (2013.01); *A61B 6/585* (2013.01); *A61B 6/588* (2013.01); *A61N 2005/105* (2013.01); *A61N 2005/1051* (2013.01); *H01J 2237/1501* (2013.01); *H01J 2237/20292* (2013.01); *H01J 2237/2482* (2013.01); *H01J 2237/24528* (2013.01); *H04B 10/22* (2013.01)

(58) Field of Classification Search
CPC ............ A61B 6/00; A61B 6/04; A61B 6/08; A61B 6/40; A61B 6/42; A61B 6/44; A61B 6/4405; A61B 6/4411; A61B 6/4429; A61B 6/4452; A61B 6/4464; A61B 6/4476; A61B 6/46; A61B 6/461; A61B 6/465; A61B 6/467; A61B 6/587; A61B 6/0492; A61B 6/547; A61B 6/585; H05G 1/00; H05G 1/02; H05G 1/08; G01N 23/00; G01N 23/02; G01N 23/04; G01N 23/06; G01N 23/08; G01N 23/083; G02B 7/00; G02B 7/003; G02B 7/005; G02B 13/00; G02B 13/16; G02B 23/00; G02B 27/00; G02B 27/40; G02B 27/64; H01J 35/00; H01J 35/02; H01J 35/025; H01J 35/14; H01J 35/16; H01J 37/22; H01J 37/244; H01J 2237/15; H01J 2237/1501; H01J 2237/1504; H01J 2237/20; H01J 2237/20292; H01J 2237/24495; H01J 2237/245; H01J 2237/24507; H01J 2237/24514; H01J 2237/24528; H01J 2237/248; H01J 2237/2482; H01J 2237/2485; H01J 2237/2487; H04B 10/114; H04B 10/1141; H04B 10/116; H04B 10/22; H04B 10/50; H04B 10/501; H04B 10/502; H04B 10/503; H04B 10/516; H04B 10/548; H04B 10/556; H04B 10/5563; H04B 10/60; H04B 10/66; H04B 15/00; G01T 1/29; G01T 1/2907; G01T 1/2914; G01T 7/01; G01T 7/005; A61N 5/00; A61N 5/01; A61N 5/1048; A61N 5/1049; A61N 5/1064; A61N 5/1065; A61N 5/1067; A61N 2005/0626; A61N 2005/0632; A61N 2005/0664; A61N 2005/105; A61N 2005/1051

See application file for complete search history.

(56) References Cited

U.S. PATENT DOCUMENTS

| | | | |
|---|---|---|---|
| 5,241,578 A * | 8/1993 | MacMahon ............ | A61B 6/587 378/154 |
| 5,729,587 A | 3/1998 | Betz | |
| 2002/0080921 A1 | 6/2002 | Smith et al. | |
| 2003/0194056 A1 | 10/2003 | Spahn | |
| 2004/0105526 A1* | 6/2004 | Zhang ................... | A61B 6/08 378/205 |
| 2004/0141590 A1* | 7/2004 | Ihalainen ................. | A61B 6/08 378/206 |
| 2005/0058256 A1* | 3/2005 | Beimler ................... | A61B 6/08 378/162 |
| 2005/0226377 A1* | 10/2005 | Wong ...................... | A61N 5/10 378/65 |

| | | | |
|---|---|---|---|
| 2007/0165775 A1* | 7/2007 | Graumann | A61B 6/4441 378/19 |
| 2008/0165933 A1* | 7/2008 | Hornig | A61B 6/08 378/206 |
| 2009/0032744 A1 | 2/2009 | Kito et al. | |
| 2010/0046705 A1 | 2/2010 | Jabri et al. | |
| 2010/0215152 A1* | 8/2010 | Takahashi | A61B 6/4429 378/197 |
| 2010/0239070 A1 | 9/2010 | Mohr | |
| 2012/0039447 A1* | 2/2012 | Lalena | A61B 6/08 378/206 |
| 2013/0114790 A1* | 5/2013 | Fabrizio | A61B 6/02 378/62 |

FOREIGN PATENT DOCUMENTS

DE 102007033235 A1 1/2009

OTHER PUBLICATIONS

Kassies, Roel et al., "Removing Optical Feedback and Interference Artifacts in AFM Measurements by Application of High Frequency Laser Current Modulation", Feb. 2004, Review of Scientific Instruments, 75(3), pp. 689-693.*

Zhang, Da, et al., "A Convenient Alignment Approach for X-ray Imaging Experiments Based on Laser Positioning Devices", Oct. 14, 2008, Am. Assoc. Phys. Med., Med. Phys. 35 (11), pp. 4907-4910.*

* cited by examiner

*Primary Examiner* — Anastasia Midkiff

(57) ABSTRACT

An X-ray imaging system includes an X-ray tube (6), a ceiling suspension (2) for the X-ray tube, a detector trolley (12) with an X-ray detector (10) mounted thereon, an active sensor matrix (24), an optical indication unit (20) and a control unit (26). The active sensor matrix (24) is fixedly mounted on the ceiling suspension (2), the optical indication unit (20) is fixedly mounted to the detector trolley (12) and is adapted for emitting an optical indication (22) onto the active sensor matrix (24). The control unit (26) is connected to the active sensor matrix (24) and is adapted for acquiring the position of the optical indication (22) on the active sensor matrix (24) and to create control signals for aligning the detector trolley position and the ceiling suspension position relative to each other.

19 Claims, 3 Drawing Sheets

CONTROL FOR OPTICALLY ALIGNING AN X-RAY TUBE AND X-RAY DETECTOR

CROSS-REFERENCE TO PRIOR APPLICATIONS

This application is the U.S. National Phase application under 35 U.S.C. §371 of International Application No. PCT/IB2012/056716, filed on Nov. 26, 2011, which claims the benefit of U.S. Provisional Patent Application No. 61/565,545, filed on Dec. 1, 2011. These applications are hereby incorporated by reference herein.

FIELD OF THE INVENTION

The present invention relates to a medical imaging system and a method for providing an x-ray image.

BACKGROUND OF THE INVENTION

For trauma x-ray application, technicians usually have to bring a detector and an X-ray tube near a patient lying on a trauma trolley in an environment with a lot of people around. A patient may be wired to medical equipment that may disturb a proper X-ray examination. Therefore, trauma X-ray applications are sophisticated.

Usually, for an X-ray examination in this environment, there are two general different workflows existing, depending on the size, shape and position of the object to be examined. In a first workflow, the X-ray tube is adjusted to the region of interest in that it is positioned to align with the outer/inner dimensions of the relevant anatomy of the patient. The detector has to be aligned according to the position of the X-ray tube in a certain predetermined "source image distance" (SID) and with the detector center aligning with a central spot of the X-rays. Therefore, the X-ray tube comprises a "master function". In a second workflow, the X-ray tube freely emits X-rays limited by a collimator to the region of interest. A portable X-ray detector is positioned relative to the region of interest. Therefore, the detector has a "master function".

For the first workflow type, the detector and the x-ray tube are mechanically linked. The detector is positioned on a mechanical arm connected to the X-ray tube. Whenever the X-ray tube is moved relative to the patient the detector follows in a predetermined distance and a fixed spatial relationship.

For the second workflow, a mechanical arm may be folded aside, thus removing the detector from its spatially fixed relationship and to use the X-ray tube for free exposures.

SUMMARY OF THE INVENTION

In trauma environments, it may be favorable to reduce the weight and bulkiness of an X-ray imaging device to make the device easier to move and to position and, further on, to reduce the occupied space near the patient. An X-ray imaging device having a foldable mechanical link between an X-ray source and a detector may obstruct some space around the patient.

Also, it may be favorable to modify or control a distance between an X-ray tube and a detector more individually for increasing the available space at the patient whenever it is necessary.

Therefore, there may exist a need for a less bulky X-ray imaging device that is easier to move and to position as commonly known X-ray trauma devices allowing free exposures when necessary and with less space obstruction.

Advantageous embodiments and further improvements can be derived from following description.

An X-ray imaging system according to the invention comprises an X-ray tube, a ceiling suspension for the X-ray tube, a detector trolley with an X-ray detector mounted thereon, an active sensor matrix, an optical indication unit and a control unit. The active sensor matrix is fixedly mounted on the ceiling suspension. The optical indication unit is fixedly mounted to the detector trolley and is adapted for emitting an optical indication onto the active sensor matrix. The control unit is connected to the active sensor matrix and is adapted for acquiring the position of an optical indication on the active sensor matrix and to create control signals for controlling at least one of the ceiling suspension and the detector trolley to adjust the position of the optical indication to the predetermined position.

The detector trolley is a cart like element that has a base, which base is adapted for supporting the trolley on a floor of an operating room. It is clear that the detector trolley is dimensioned such that the detector attached to it may be moved under the trauma trolley without colliding with any element of the trauma trolley. In the light of the invention, it becomes clear that the detector trolley comprises drive means and/or actuating means that can be triggered by control signals for moving the detector trolley on the floor of the operating room.

The ceiling suspension supports the X-ray tube and is equipped with drive/actuating means for moving the X-ray tube at least along a plane parallel to the ceiling. Preferably, the X-ray tube may also be adjusted in a distance to the ceiling, thereby adjusting the distance between the detector and the X-ray source (SID). The drive means may be triggered by control signals.

As the optical indication unit emits an optical indication onto the active sensor matrix the control unit then can detect the relative position of the X-ray source and the detector. If a desired relative position between the detector and the X-ray source is predefined the control unit is enabled to determine the deviation/difference between the predefined position of the detector relative to the X-ray source by acquiring the position of the emitted optical indication on the active sensor matrix and compare it to the predefined position. The control unit may then create control signals that are transferred to the detector trolley and/or the ceiling suspension. For example, a first command may be generated that is transferred to the detector trolley to adjust the detector trolley position. A second command may be generated that is transferred to the ceiling suspension to adjust the ceiling suspension position. Based on predetermined control laws, either the ceiling suspension device or the detector trolley are moved by means of the integrated drive/actuating means to the predefined relative position.

With this setup it is easily possible to automatically link the positions of the X-ray tube and the detector trolley. Even without a direct mechanical link between the detector trolley and the X-ray source, the relative position can very precisely be determined.

For example, the optical indication may be realized as a light emitting means, such as a laser or similar devices, emitting a light beam in the visible or invisible frequency range. Preferably the emitted light beam has a fan shape so that the optical indication overlaps a plurality of active sensors, thus enhancing the determination of a motion, a motion direction and a velocity. A rotation of the detector trolley relative to the ceiling suspension can furthermore only be detected when the fan shape is designed such that it is not completely symmetrical.

The positioning process in the system is always systemic. A "master function" of the X-ray tube or the detector is not mandatory any more. It is useful to control the positioning process by moving the detector trolley alone leading to a synchronous motion of the X-ray tube as if the X-ray tube was a master, since the clinician checks the positioning by means of the light field of the X-ray tube, but the motion itself is initiated at the detector.

Furthermore in order to initiate an imaging function for the desired region of interest on the patient the clinician may also move the X-ray tube to the desired position and initiate a position adjustment or a positioning link of the detector trolley. In both cases the control unit aquires the relative position of the detector trolley to the X-ray source and automatically adjusts the position through control signals sent to the ceiling suspension or detector trolley. It may be sensible to use the control of the detector trolley for a fine tuning of the detector trolley position.

It is furthermore conceivable that the clinician positions the X-ray tube by a handle or the such and still manually positions the detector trolley afterwards, but without a link between the X-ray tube and the detector trolley. The orientation of the detector relative to the X-ray tube may be checked on a display unit placed in the vicinity of the clinician.

A collimator may be adjusted by means of manual control means.

In an advantageous embodiment, the active sensor matrix comprises an array of sensitive elements that detect the presence of the optical indication. The sensitive elements are preferably arranged in a matrix shape and are adapted for detecting an impinging optical indication. The active sensor matrix may output a signal that either comprises position and motion information that are already interpreted from the impinging optical indication or raw data comprising strength and/or brightness information of each of the sensitive elements for interpretation through the control unit.

As mentioned above the optical indication on the active sensor matrix may have a dimension exceeding the dimension of a sensitive element, thus enabling an overlap of the optical indication on a plurality of sensitive elements.

In an advantageous embodiment, the sensitive elements are selected from a group of sensitive elements the group comprising an array of photo diodes, a CMOS array and a CCD array. Using photo diodes may be rather cost effective but CMOS and CCD arrays may increase the position detection and therefore the precision of the detector trolley position. Furthermore, many similar sensitive elements may be chosen without departing from the scope of the invention.

In an advantageous embodiment the optical indication is positioned perpendicular to the base of the detector trolley. Thereby, the position of the optical indication on the ceiling suspension device matches with the position of the detector trolley on the floor in the operating room.

In a further advantageous embodiment the optical indication is adapted for overlaying a HF-pattern to the optical indication for avoiding disturbances from other sources and wherein at least one of the active sensor matrix and the control unit is adapted for recognizing the overlaid HF-pattern. In case the control unit acquired raw data from the active sensor matrix the control unit has to interpret the data so as to detect a predefined HF-pattern. On the other hand the active sensor matrix may also comprise an electronics unit that is adapted for interpreting raw data of the sensitive elements and recognizing HF-patterns and merely outputs position and motion information.

Preferably the HF pattern is realized as a series of light pulses with at least one predetermined frequency for enabling an identifiable optical indication. It is further conceivable to use a plurality of frequencies in order to increase the robustness of the identification process for the optical indication.

In a further advantageous embodiment the X-ray tube is integrated into a housing comprising a display for displaying an alignment status for the X-ray tube and the detector trolley relative to each other. Thereby a visual aid is provided for a clinician.

In an advantageous embodiment the detector trolley comprises a data link for transferring control data between the detector trolley and the control unit, thereby enabling the detector trolley to emit control data necessary or optional for controlling the system as a whole, to initiate a link between a detector position and an X-ray source position and to receive control signals for following the position of the X-ray tube.

In a further advantageous embodiment, the imaging system comprises a detector trolley user interface having input means for controlling the ceiling suspension, wherein the trolley user interface is connected to the data link. It is preferred that the detector trolley user interface comprises at least one "attached"-button to synchronize the detector trolley and the ceiling suspension movements especially for cases where the detector trolley is moved by a clinician to a desired position and the X-ray tube shall be automatically adjusted to the detector trolley position. Further on, collimation wheels for adjusting the size of the collimator should be integrated as well as a source image distance button for changing the SID to e. g. 110 or 150 cm.

In an advantageous embodiment the optical indication unit is integrated into the detector trolley user interface, which user interface is fixedly mounted to the detector trolley. Thereby separate supports for separate units can be eliminated and the system has an even lower complexity and bulkiness.

In an advantageous embodiment the data link is a wireless data link for eliminating the cables to avoid injuries in the operating room.

According to a further aspect of the invention there is provided a method for providing an X-ray image comprising the following steps:

Emitting an optical indication from an optical indication unit fixedly mounted on a detector trolley onto an active sensor matrix, acquiring a position of the optical indication on the active sensor matrix, comparing the acquired position with a predetermined position and generating control signals for controlling at least one of a ceiling suspension and the detector trolley to adjust the position of the optical indication to the predetermined position. These steps enable a direct link of the detector trolley and the ceiling suspension positions in both possible workflows.

In an advantageous embodiment, the control signal is transferred to the detector trolley for adjusting the detector trolley position on receiving a first command. This may be conceivable for fine tuning of the detector trolley position on slight adjustments conducted directly on the X-ray tube.

In a further advantageous embodiment, the control signal is transferred to the ceiling suspension on receiving a second command. The second command may be initiated by input means present on the detector trolley as described further above.

A further advantageous embodiment may comprise overlaying a HF pattern to the optical indication for avoiding disturbances from other sources, as explained further above.

It has to be noted that features and side effects of the present invention have been described with reference to different embodiments of the invention. However, a person skilled in the art will gather from the above and the following description that unless other notified in addition to any combination or features belonging to one embodiment also any combinations between features relating to different embodiments or to a manufacturing method is considered to be disclosed with this application.

BRIEF DESCRIPTION OF THE DRAWINGS

The features and embodiments defined above and further features and advantages of the present invention can also be derived from the examples of embodiments to be described herein after and are explained with reference to examples of embodiments, but to which the invention is not limited. The invention will be described in more detail hereinafter with reference to the drawings.

DETAILED DESCRIPTION OF EMBODIMENTS

Figure 1:
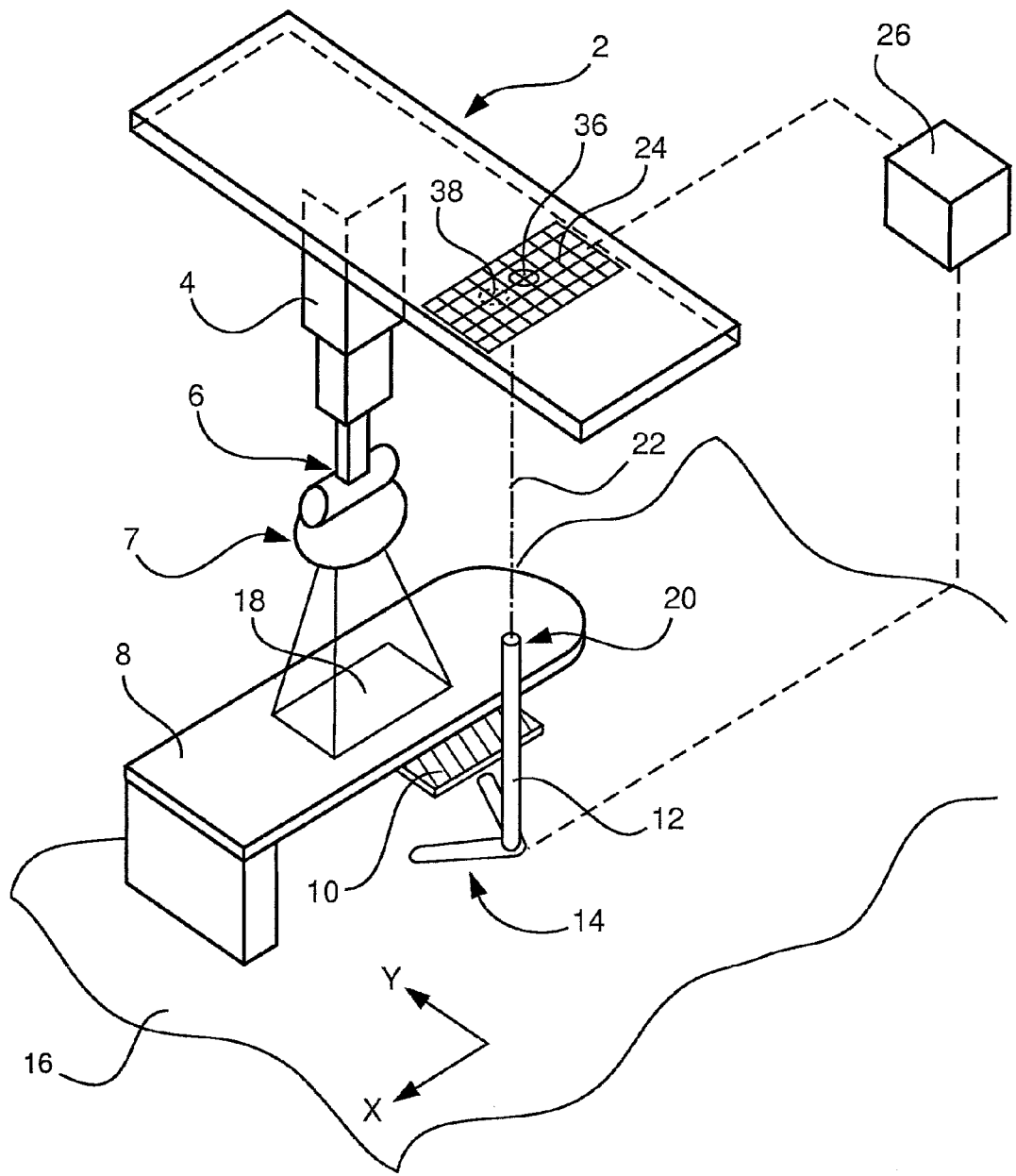
FIG. 1 shows an overview of the system for providing an X-ray image.

FIG. 1 shows an overview of the system according to the invention. A ceiling suspension 2 supports an X-ray tube arm 4 and comprises at least one actuating/drive means for moving the X-ray tube arm 4 along the ceiling in X- and Y-direction. The tube arm 4 itself holds the X-ray tube 6 adapted for emitting X-ray beams to a patient trolley 8 present below the X-ray tube. The patient trolley 8 itself does not constitute a part of the system according to the invention and is merely displayed for illustration purposes.

A detector 10 is mounted to a detector trolley 12, which detector trolley has a base 14 movable in X- and Y-direction on the floor 16. The detector 10 can thereby be moved under the trauma trolley 8 and thereby move into and out of a region of interest 18.

For attaching or linking the position of the detector 10 to the position of the X-ray tube 6, an optical indication unit 20 is fixedly mounted on the detector trolley 12 for emitting an optical indication 22 onto an active sensor matrix 24 that is fixedly mounted on the ceiling suspension 2. The optical indication unit 20 is aligned such that it emits the optical indication 22 perpendicularly to the floor 16. Thereby, the position of the optical indication 22 on the active sensor matrix 24 conforms the actual detector trolley position.

A control unit 26 is connected to the active sensor matrix 24 and therefore adapted to acquire the actual position of the detector trolley 12 relative to the ceiling suspension 2. The control unit 26 is depicted in a schematic manner as it may be integrated into the ceiling suspension, the tube arm 4, a housing of the X-ray tube 6, the detector trolley 12 or another electronics unit not shown in FIG. 1. In the following it is assumed that the control unit 26 is not integrated into the detector trolley 12.

If the detector trolley 12 is to follow the position of the X-ray tube 6, preferably for a fine tuning of the detector trolley position, a deviation between the predetermined position on the active sensor matrix 24 and the actual position of the optical indication 22 can be interpreted as a control variable. Using a suitable control law, the control unit 24 can create control signals for triggering a drive / actuation means in the detector trolley 12 in order to link the position of the detector trolley 12 to the position of the X-ray tube 6. In an alternate control mode, the control unit 26 may attach the position of the ceiling suspension 2 by transferring the generated control signals to the ceiling suspension 2 to adjust its position to the actual position of the detector trolley 12. The X-ray tube 6 is integrated into a housing comprising a display 7 for displaying an alignment status for the X-ray tube 6 and the detector trolley 12 relative to each other.

Figure 2:
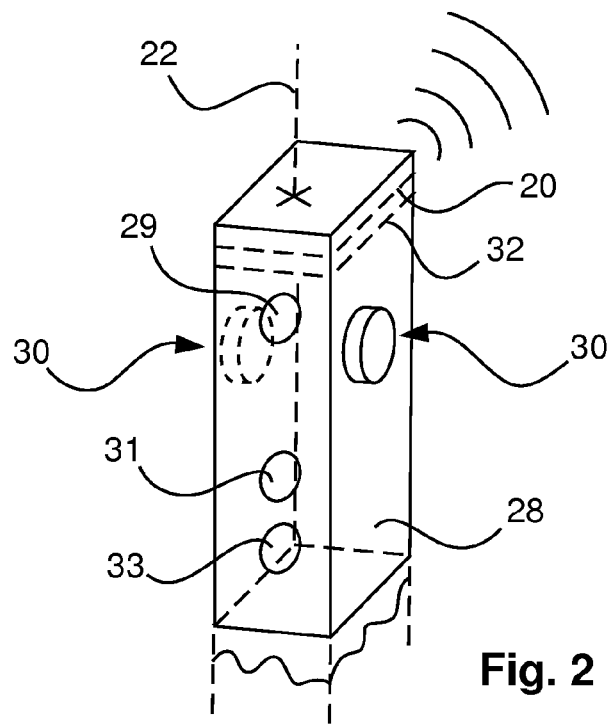
FIG. 2 shows a detail of the detector trolley.

As depicted in FIG. 2 a trolley user interface 28 is attached to the detector trolley 12 and comprises a set of user input devices. E.g. a button 29 may be dedicated to the attaching function for linking a position of the detector trolley 12 to a position of the ceiling suspension 2. Preferably two controllers 30 may be used for the adjustment for a collimator (not shown) and buttons or other input devices 31 and 33 provide for an adjustment of the source image distance (SID) to either e.g. 110 or 150 cm.

The detector trolley user interface 28 may integrate the optical indication unit 20 and may further be equipped with a data link unit 32 for wirelessly connecting to the control unit 26 for transferring commands to the control unit 26 or to receive control signals for adjusting the position.

Figure 3A:
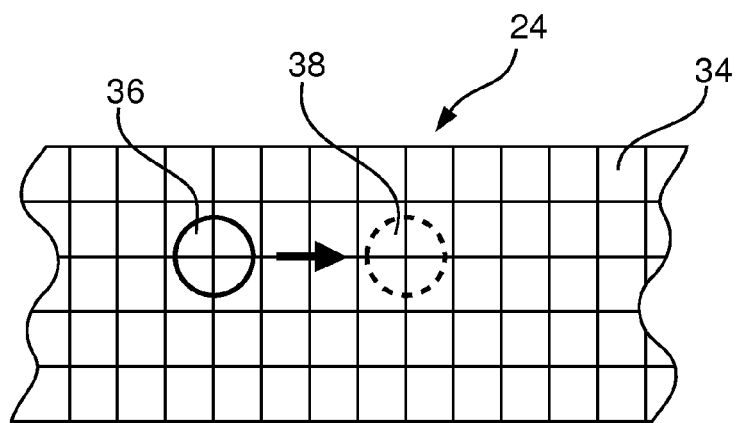
FIGS. 3a and 3b show a schematic drawing of an optical indication on the active sensor matrix with different optical indications.

FIG. 3a shows a section of an active sensor matrix 24, comprising an array of sensitive elements 34. The optical indication 22 impinges onto the active sensor matrix 24 and thereby may overlap a plurality of sensitive elements 34 under creation of an indication spot 36. A predetermined indication spot position 38 of the optical indication is symbolized by a dashed circle. As the control unit 26 has information about a predetermined spot position 38, it is enabled to compare the predetermined spot position 38 and the actual position of the optical indication and thereby generate control signals for removing the deviation.

Figure 3B:
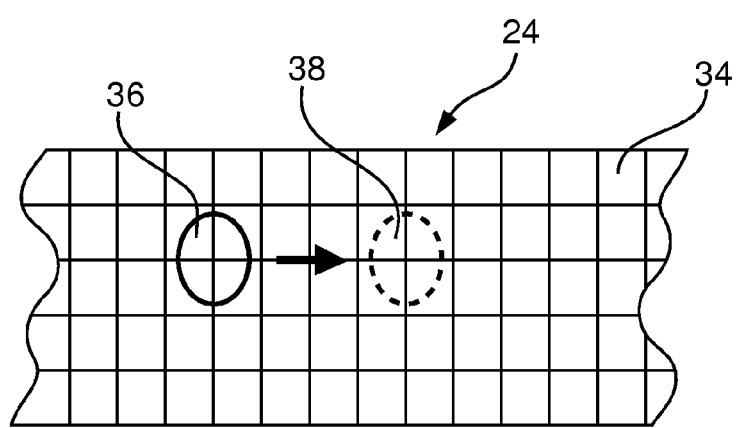

As FIG. 3a shows circular indication spots 36 and 38 these may also by less symmetrical, e.g. comprising elliptical or other shapes, demonstrated in FIG. 3b. Thereby, the rotational orientation of the detector trolley 12 relative to the ceiling suspension can be easily acquired.

Figure 4:
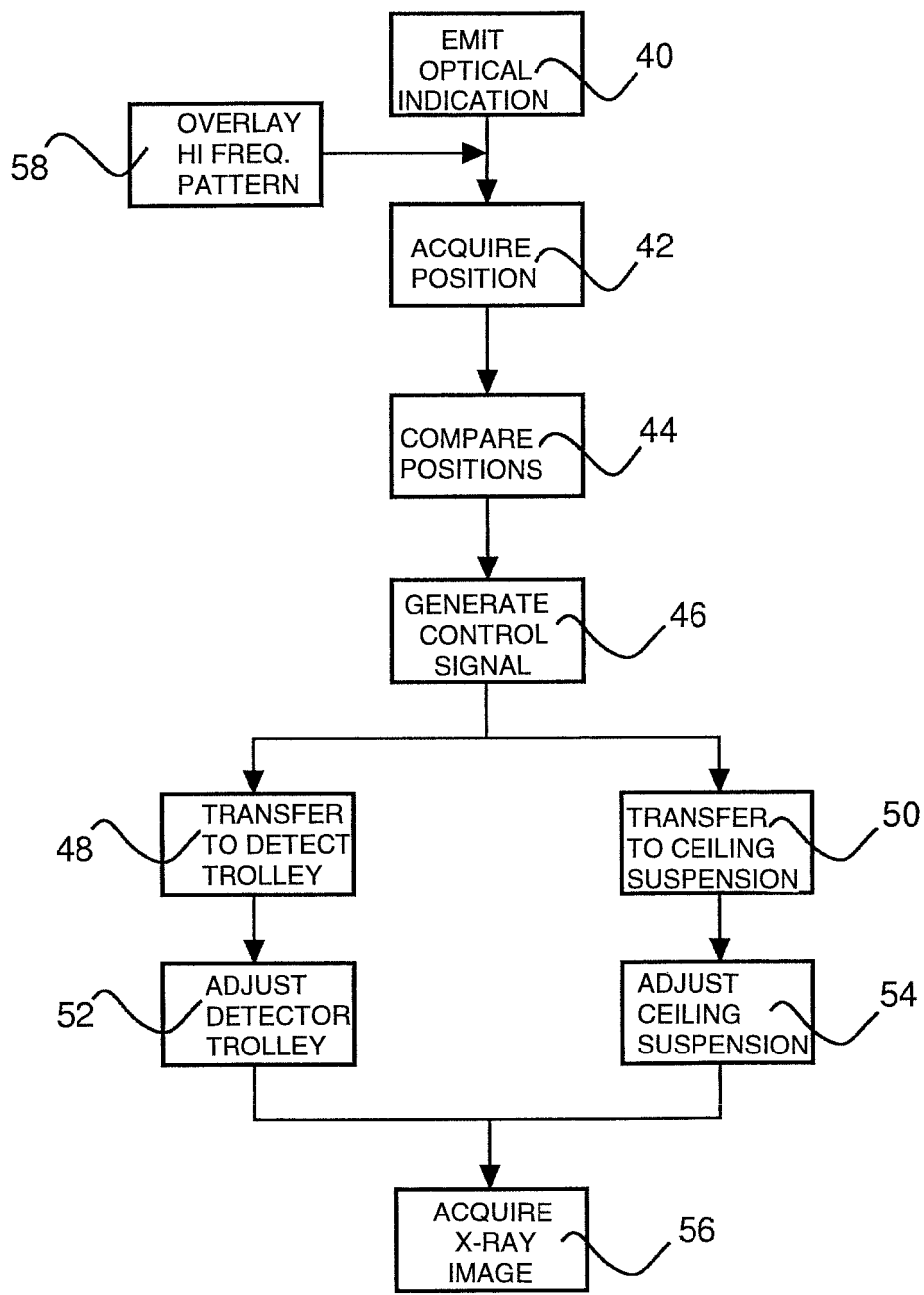
FIG. 4 shows a schematic drawing of the method for providing an X-ray image. The figures are only schematically and not to scale.

Finally, FIG. 4 shows a block diagram of a method for providing an X-ray image, comprising the steps of emitting 40 an optical indication from an optical indication unit fixedly mounted on a detector trolley onto an active sensor matrix, acquiring 42 a position of the optical indication on the active sensor matrix, comparing 44 the acquired position with a predetermined position and generating 46 control signals for controlling at least one of a ceiling suspension and the detector trolley to adjust the position of the optical indication to the predetermined position. The control signal may be transferred 48 to the detector trolley for adjusting 52 the detector trolley position on receiving a first command or may be transferred 50 to the ceiling suspension for adjusting 54 the ceiling suspension position on receiving a second command. Afterwards, the X-ray image may be acquired 56.

In order to improve the robustness of the optical indication and the detection thereof a HF pattern may be overlaid 58 to the optical indication.

Finally, it is to be noted that herein the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging system, comprising
an X-ray tube
a ceiling suspension for the X-ray tube,
a detector trolley with an X-ray detector mounted thereon,
an active sensor matrix,
an optical indication unit and
a control unit,
wherein the active sensor matrix is fixedly mounted on the ceiling suspension,
wherein the optical indication unit is fixedly mounted to the detector trolley and is adapted for emitting an optical indication onto the active sensor matrix,
wherein the control unit is connected to the active sensor matrix and is adapted for acquiring the position of the optical indication on the active sensor matrix, for comparing the acquired position with a predetermined position, and for creating control signals for controlling at least one of the ceiling suspension and the detector trolley to adjust the position of the optical indication to the predetermined position.

2. The X-ray imaging system according to claim 1, wherein the active sensor matrix comprises an area of sensitive elements that are mounted stationarily relative to a ceiling and that detect the optical indication.

3. The X-ray imaging system according to claim 2, wherein the sensitive elements are selected from a group of sensitive elements, the group comprising:
a matrix of photodiodes,
a CMOS matrix and
a CCD matrix.

4. The X-ray imaging system according to claim 1, wherein the detector trolley has a base configured to move horizontally over a floor;
wherein the X-ray detector is fixedly mounted on the detector trolley; and
wherein the optical indication unit is configured to emit a light beam perpendicularly to a floor.

5. The X-ray imaging system according to claim 1, wherein the optical indication unit includes a laser configured to emit the optical indication as a light beam in an invisible frequency range.

6. The X-ray imaging system according to claim 1, wherein the X-ray tube is integrated into a housing comprising a display for displaying an alignment status for the X-ray tube and the detector trolley relative to each other.

7. The X-ray imaging system according to claim 1, wherein the detector trolley comprises a data link unit for transferring control data between the detector trolley and the control unit.

8. The X-ray imaging system according to claim 7, further comprising a detector trolley user interface having input means for controlling the ceiling suspension, wherein the detector trolley user interface is connected to the data link unit.

9. The X-ray imaging system according to claim 8, wherein the optical indication unit is integrated into the detector trolley user interface, which user interface is fixedly mounted to the detector trolley.

10. The X-ray imaging system according to claim 7, wherein the data link unit is a wireless data link.

11. A method for positioning an X-Ray detector mounted on a detector trolley relative to an X-ray tube movably mounted on a ceiling suspension,the detector tolley being configured to move over a floor, the method comprising:
emitting an optical indication from an optical indication unit fixedly mounted on the movable detector trolley onto an active sensor matrix fixedly mounted relative to a ceiling,
acquiring a position of the optical indication on the active sensor matrix,
comparing the acquired position with a predetermined position and
generating control signals for controlling at least one of the ceiling suspension to move the X-ray tube relative to the ceiling and the active sensor matrix and the detector trolley over the floor to adjust the position of the optical indication to the predetermined position.

12. The method according to claim 11, further comprising:
transferring the control signal to the detector trolley for adjusting the detector trolley position.

13. The method according to claim 11, further comprising:
transferring the control signal to the ceiling suspension for controlling a drive to adjust a position of the X-ray tube relative to the ceiling on receiving a command.

14. The X-ray imaging system according to claim 1, wherein the ceiling suspension supports an X-ray tube arm which carries the X-ray tube and wherein the ceiling suspension includes a drive for moving the X-ray tube arm relative to the ceiling suspension; and
wherein the trolley and the affixed optional indication unit are configured to move over a floor.

15. The X-ray imaging system according to claim 1, wherein the X-ray detector is fixedly mounted to the detector trolley such that the detector trolley and the affixed X-ray detector and the affixed optical indication unit move as a unit.

16. The X-ray imaging system according to claim 1, wherein the control unit is configured to align the X-ray tube and the X-ray detector.

17. An X-ray imaging system comprising:
a ceiling suspension configured to be mounted to a ceiling of an imaging area, the ceiling suspension including a drive;
an X-ray arm mounted to the ceiling suspension and configured to be moved relative to the ceiling suspension in horizontal directions by the drive;
an X-ray tube supported by the X-ray arm;
an active sensor matrix fixedly mounted to the ceiling suspension;
a detector trolley configured to move over a floor of the imaging area in horizontal directions;
an X-ray detector fixedly mounted to the detector trolley;
a light source fixedly mounted to the detector trolley and configured to emit a light beam directed to the active sensor matrix;
a controller connected with the active sensor matrix to acquire a position of the light beam on the active sensor matrix, the controller configured to compare the acquired light beam position with a predetermined position and generate drive signals to at least one of the ceiling suspension drive and the detector trolley to align a relative position of the light beam with the predetermined position.

18. The X-ray imaging system according to claim 17, further including a detector trolley user interface fixedly mounted to the detector trolley, the detector trolley interface including a user input for controlling the ceiling suspension drive.

19. The X-ray imaging system according to claim 18, further including a display integrated into a housing of the X-ray tube, the display being configured to display an alignment status for the X-ray tube and the X-ray detector relative to each other.

* * * * *